United States Patent
Dressman et al.

(10) Patent No.: US 9,212,129 B2
(45) Date of Patent: Dec. 15, 2015

(54) METABOLITES OF (1R-TRANS)-N-[[2-(2,3-DIHYDRO-4-BENZOFURANYL)CYCLOPROPYL]METHYL]PROPANAMIDE

(71) Applicant: Vanda Pharmaceuticals, Inc., Washington, DC (US)

(72) Inventors: Marlene Michelle Dressman, Germantown, MD (US); Deepak Phadke, Olathe, KS (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 0 days.

(21) Appl. No.: 14/401,857

(22) PCT Filed: May 17, 2013

(86) PCT No.: PCT/US2013/041573
§ 371 (c)(1),
(2) Date: Nov. 18, 2014

(87) PCT Pub. No.: WO2013/173707
PCT Pub. Date: Nov. 21, 2013

(65) Prior Publication Data
US 2015/0148419 A1     May 28, 2015

Related U.S. Application Data

(60) Provisional application No. 61/649,220, filed on May 18, 2012.

(51) Int. Cl.
*A61K 31/133* (2006.01)
*C07C 233/18* (2006.01)
*C07C 233/47* (2006.01)
*C07C 233/25* (2006.01)

(52) U.S. Cl.
CPC ............. *C07C 233/47* (2013.01); *C07C 233/18* (2013.01); *C07C 233/25* (2013.01); *C07B 2200/13* (2013.01)

(58) Field of Classification Search
CPC ....................................................... C07C 233/18
See application file for complete search history.

(56) References Cited

U.S. PATENT DOCUMENTS 5,856,529 A     1/1999 Catt et al.

FOREIGN PATENT DOCUMENTS

| WO | 9825606 A1 | 6/1998 |
| WO | 03037337 A1 | 5/2003 |
| WO | 2004006886 A2 | 1/2004 |

OTHER PUBLICATIONS

Rajaratnam et al., "Melatonin agonist tasimelteon (VEC-162) for transient insomnia after sleep-time shift: Two randomised controlled multicentre trials," 2009, pp. 482-491, The Lancet, vol. 373, No. 9662 (XP025913508).
Srinivasan et al., "Melatonin agonists in primary insomnia and depression-associated insomnia: Are they superior to sedative-hypnotics?," 2011, pp. 913-923, Progress in Neuro-Psychopharmacology & Biological Psychiatry, vol. 35, No. 4 (XP028211980).
Vachharajani et al., "Preclinical Pharmacokinetics and Metabolism of BMS-214778, a Novel Melatonin Receptor Agonist," 2003, pp. 760-772, Journal of Pharmaceutical Sciences, vol. 92, No. 4 (XP008074135).
Hardeland, "New approaches in the management of insomnia: Weighing the advantages of prolonged-release melatonin and synthetic melatoninergic agonists," 2009, pp. 341-354, Neuropsychiatric Disease and Treatment, Dovepress Medical Press (NZ) Ltd., vol. 5, No. 1 (XP009137641).
Liang et al., "Simultaneous Determination of Tasimelteon, M9, M11, M12, M13, and M14 in Human Plasma by UPLC-MS/MS and its Applications," 2012, 1 page, retrieved from: http://www.qps.com/posters/HL_ASMS2012Poster_05_11_2012.pdf (XP50067652).
Patent Cooperation Treaty, The International Search Report and the Written Opinion of the International Searching Authority, or the Declaration for PCT/US2013/041573 dated Aug. 12, 2013, 16 pages.

*Primary Examiner* — Samantha Shterengarts
(74) *Attorney, Agent, or Firm* — Hoffman Warnick LLC

(57) ABSTRACT

Isolated metabolites of (1R-trans)-N-[[2-(2,3-dihydro-4-benzofuranyl)cyclopropyl]-methyl]propanamide, methods for their use, and compositions containing the metabolites.

12 Claims, No Drawings

METABOLITES OF (1R-TRANS)-N-[[2-(2,3-DIHYDRO-4-BENZOFURANYL)CYCLOPROPYL]METHYL] PROPANAMIDE

CROSS-REFERENCE TO RELATED APPLICATIONS

This application claims the benefit of co-pending U.S. Provisional Patent Application No. 61/649,220, filed 18 May 2012, which is hereby incorporated herein.

TECHNICAL FIELD

The invention relates to metabolites of (1R-trans)-N-[[2-(2,3-dihydro-4-benzofuranyl)cyclopropyl]methyl]propanamide and their uses.

BACKGROUND OF THE INVENTION (1R-trans)-N-[[2-(2,3-dihydro-4-benzofuranyl)cyclopropyl]methyl]propanamide, a specific and potent agonist of the MT1R and MT2R melatonin receptors in the suprachiasmatic nucleus (SCN), is described in U.S. Pat. No. 5,856,529, which is incorporated herein by reference as though fully set forth. Engagement of the MT1R and MT2R receptors by melatonin is believed to regulate circadian rhythms, including the sleep/wake cycle. (1R-trans)-N-[[2-(2,3-dihydro-4-benzofuranyl)cyclopropyl]methyl]-propanamide is well-tolerated and demonstrates potent chronobiotic activity in preclinical models of acute phase-shifting and chronic re-entrainment.

SUMMARY OF THE INVENTION

The invention provides metabolites of (1R-trans)-N-[[2-(2,3-dihydro-4-benzofuranyl)cyclopropyl]methyl]propanamide, methods for their use, and compositions containing the metabolites. The metabolites include a phenol-carboxylic acid analog (M9) and a hydroxypropyl-phenol analog (M11). Each is formed in humans following oral administration of (1R-trans)-N-[[2-(2,3-dihydro-4-benzofuranyl)cyclopropyl]methyl]propanamide.

Aspects of the invention include isolated compounds of Formulas II and III, including salts, solvates, and hydrates thereof, in amorphous or crystalline form. By "isolated" is meant that the compounds are isolated from human plasma or are synthetically derived.

Formula II

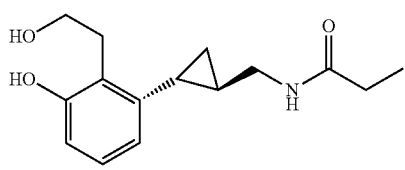

(M11)

Formula III

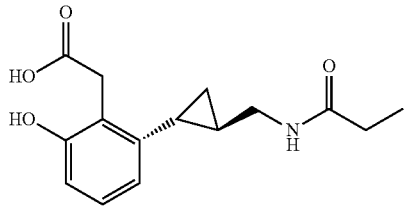

(M9)

While depicted herein in the R-trans configuration, the invention nevertheless comprises stereoisomers thereof, i.e., R-cis, S-trans, and S-cis. In addition, the invention comprises prodrugs of compounds of Formulas II and III, including, for example, esters of such compounds, as well as their administration to an individual in an amount effective to treat or prevent a sleep disorder in the individual.

Another aspect of the invention includes a pharmaceutical composition comprising at least one of the compounds above and a pharmaceutically-acceptable carrier.

Yet another aspect of the invention includes a method of treating or preventing a sleep disorder in an individual, the method comprising: directly administering to the individual an effective amount of at least one of the compounds above. By "directly" is meant that the compound is not delivered indirectly such as by administration of (1R-trans)-N-[[2-(2,3-dihydro-4-benzofuranyl)cyclopropyl]methyl]propanamide.

Still another aspect of the invention includes a method of treating or preventing a circadian rhythm disorder or disorder with a circadian component in an individual, the method comprising: directly administering to the individual an effective amount of at least one of the compounds above.

The illustrative aspects of the present invention are designed to solve the problems herein described and other problems not discussed, which are discoverable by a skilled artisan.

These and other features of this invention will be more readily understood from the following detailed description of various aspects of the invention.

DETAILED DESCRIPTION OF THE INVENTION

As noted above, the invention is directed toward isolated human metabolites of (1R-trans)-N-[[2-(2,3-dihydro-4-benzofuranyl)cyclopropyl]methyl]propanamide and their uses. Formula I, below, shows the structure of (1R-trans)-N-[[2-(2,3-dihydro-4-benzofuranyl)cyclopropyl]methyl]propanamide, herein sometimes referred to as Tasimelteon.

Formula I

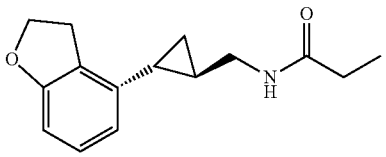

In humans, and without intending to be bound to this explanation, it appears that Tasimelteon is metabolized directly to M9 and to M11. M11 appears to be further metabolized to M9.

Oxidative dealkylation results in the opening of the furan ring of (1R-trans)-N-[[2-(2,3-dihydro-4-benzofuranyl)cyclopropyl]methyl]propanamide to yield metabolite M11, the structure of which is shown below in Formula II.

Formula II

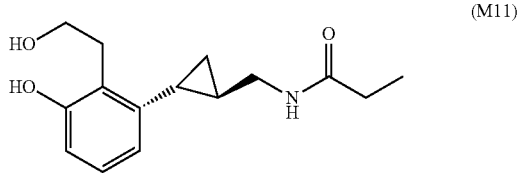

Further oxidation yields metabolite M9, a phenol-carboxylic acid derivative of (1R-trans)-N-[[2-(2,3-dihydro-4-benzofuranyl)cyclopropyl]methyl]propanamide, the structure of which is shown below in Formula III. The M9 metabolite may be formed from the M11 metabolite.

Formula III

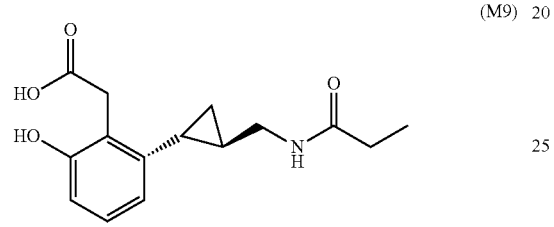

The present invention includes the isolated compounds in Formulas II and III, salts, esters, solvates, hydrates, enantiomers, stereoisomers, amorphous and crystalline forms thereof, pharmaceutical compositions containing such compounds, and methods for the use of such compounds and pharmaceutical compositions. As such, references to compounds of Formula II or III include salt, ester, solvate, hydrate, enantiomer, stereoisomer, amorphous, and crystalline forms thereof.

$^{14}$C-radiolabeled (1R-trans)-N-[[2-(2,3-dihydro-4-benzofuranyl)cyclopropyl]methyl]propanamide was administered to healthy male subjects at a dosage of 100 μCi/100 mg. Plasma, urine, and fecal samples were then collected from subjects at predetermined time intervals following administration (0.5 h, 1 h, 2 h, 8 h, and 24 h for plasma; 0-6 h, 6-12 h, 12-24 h, and 24-72 h for urine; and 0-24 h, 24-48 h, and 48-120 h for feces). Plasma and fecal samples were subjected to methanol extraction to remove proteins. All samples were centrifuged to remove solids prior to HPLC radio-chromatography. Radioactivity in each fraction was determined by Packard TopCount® NXT™ Microplate Scintillation and Luminescence Counter technology. Selected urine, plasma, and fecal extracts were analyzed by LC/MS, coupled with a radioactivity monitor.

The proportionate presence of (1R-trans)-N-[[2-(2,3-dihydro-4-benzofuranyl)cyclopropyl]methyl]propanamide and the M9 and M11 metabolites in plasma, urine, and feces of the subjects is shown below in Table 1.

TABLE 1

Tasimelteon and Select Metabolites in Plasma, Urine, and Feces

| compound | plasma (% AUC) | urine (0-72 h) (% dose) | feces (0-120 h) (% dose) | total excreta (% dose) |
|---|---|---|---|---|
| Tasimelteon | 8.22 | not detected | 0.04 | 0.04 |
| M9 | 19.79 | 29.69 | 0.85 | 30.54 |
| M11 | 3.56 | not detected | not detected | not detected |

As can be seen the M9 metabolite is a major circulating metabolite, accounting for nearly 20% of the total plasma radioactivity. Unchanged Tasimelteon (approximately 8%) and metabolite M11 (approximately 3.5%) were also detected in plasma samples. (The remaining plasma radioactivity was found in other metabolites, which are not shown.)

Neither unchanged Tasimelteon nor metabolite M11 were found in the 0-72 h urine samples. Metabolite M9, comprising nearly 30% of the radioactivity of the administered dose, represents a major urinary metabolite. Only unchanged Tasimelteon and metabolite M9 were found in fecal samples, both representing minor fecal metabolites. All fecal metabolites accounted for less than 1% of the radioactivity of the administered dose.

The M9 and M11 metabolites may also be synthesized. Specifically, the M11 metabolite may be synthesized from Tasimelteon and the M9 metabolite may be synthesized from the M11 metabolite. Synthesis pathways for the production of the M11 and M9 metabolites are shown below in Equations 1 and 2, respectively.

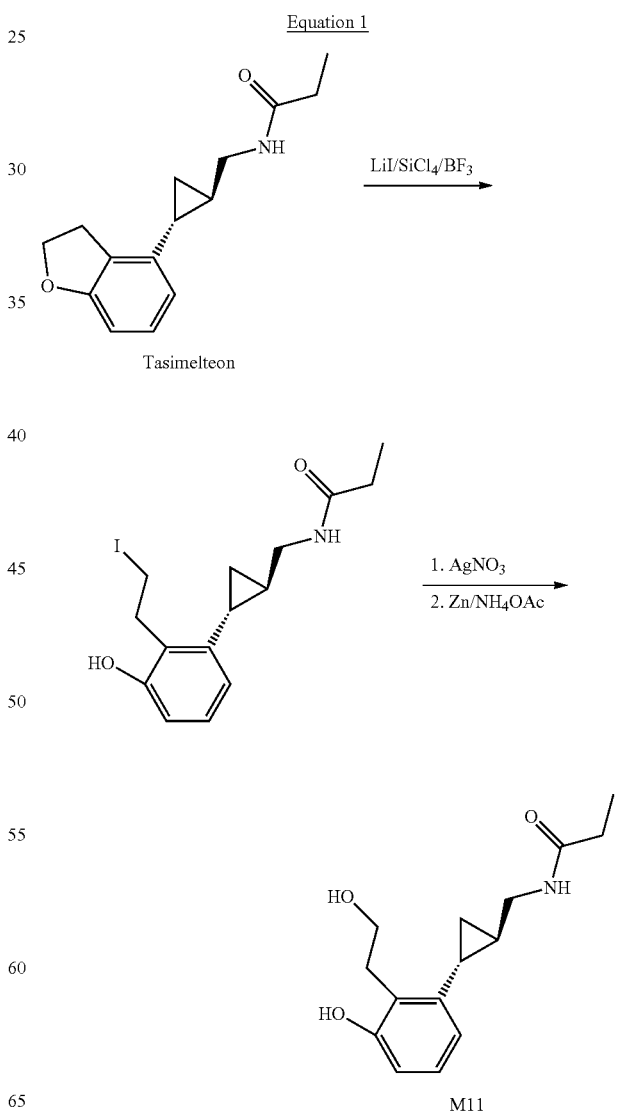

Equation 1

Equation 2

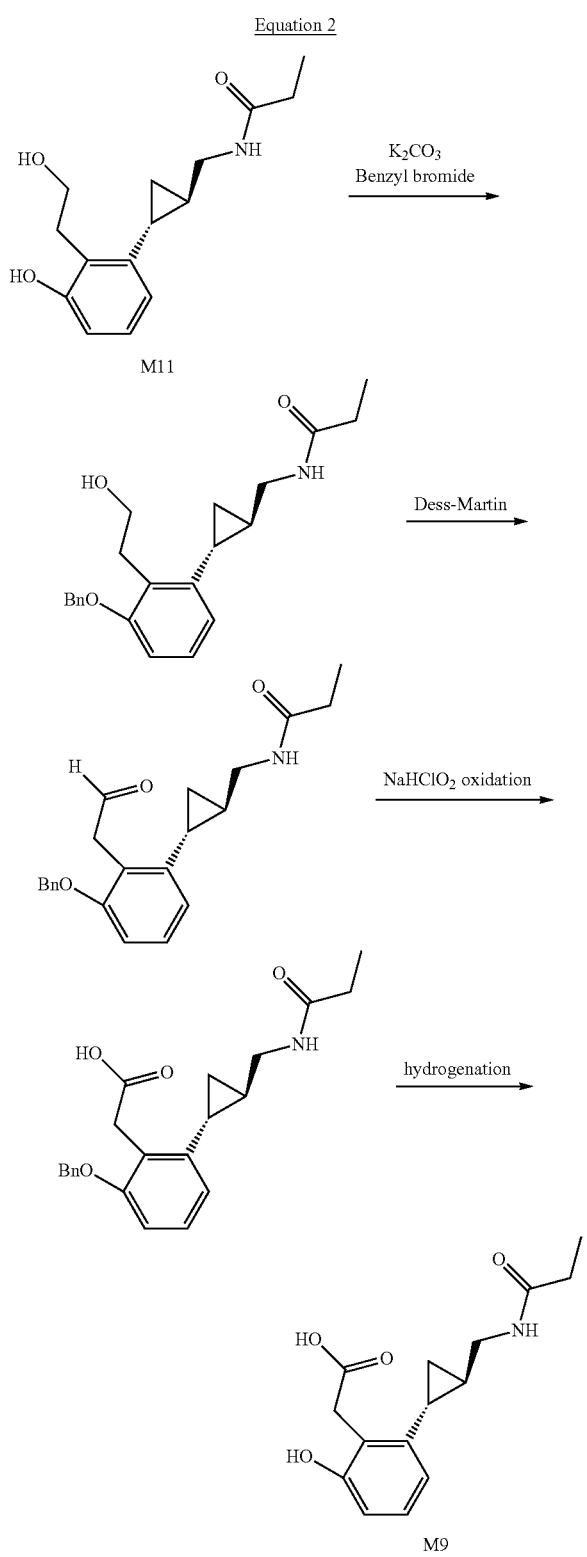

Compositions according to the invention are usually administered orally, although other routes of administration, e.g., parenteral, intravenous, intramuscular, buccal, lozenge, transdermal, transmucosal, etc., may also be used. Controlled release forms, e.g., sustained, pulsatile, or delayed, including depot forms, may also be used. Illustrative forms include those disclosed in WO2003037337 and WO2004006886, with respect to Tasimelteon and are incorporated herein. Oral unit dosage forms according to the invention typically contain between about 5 mg and about 100 mg of compounds of Formulas II and III.

An "effective amount," as that phrase is used herein, comprises a quantity sufficient to produce a desired prophylactic or therapeutic effect, whether administered alone or in combination with an adjunct. Such an effective amount will vary, depending, for example, on the severity of the disorder or symptom being treated, the individual to whom the composition is administered, the composition itself, and its route of administration. In general, the dose of compounds of formulas II and III will be in the range of about 1 mg/day to about 500 mg/day, e.g., about 10 mg/day to about 100 mg/day. Such dosages may be in one or more unit dosage forms.

It will be understood that the dosing protocol, including the amount(s) of compounds of formulas II and/or III actually administered, will be determined by a physician in light of the relevant circumstances, including, for example, the condition to be treated, the chosen route(s) of administration, the age, weight, and response of the individual to whom the compound(s) are administered, and the severity of the individual's symptom(s).

The compounds of Formulas II or III will normally be administered as a pharmaceutical composition comprising as the (or an) essential active ingredient at least one such compound in association with a solid or liquid pharmaceutically-acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions may be prepared by conventional techniques appropriate to the desired preparation containing appropriate amounts of the compounds of Formulas II or III. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum *acacia*, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compounds of the present invention may be used in the treatment or prevention of circadian rhythm disorders and/or disorders with a circadian component, sleep disorders, and any other disorder for which a melatonin agonist is indicated. Such circadian rhythm disorders and/or disorders with an underlying circadian component include jet lag, shift worker sleep disorder (SWSD), General Anxiety Disorder, Major Depressive Disorder, Seasonal Affective Disorder, Attention Deficit/Hyperactivity Disorder, Alzheimers Disease, Angelman Syndrome, Bipolar Disorder, Schizophrenia, Autism, Epilepsy, Migraine, night-time hypertension, obesity and/or type 2 diabetes, Oncology, and testosterone insufficiency. Sleep disorders which may be treated or prevented include, for example, insomnia, poor total sleep time (rapid eye movement (REM) sleep plus non-REM (NREM) sleep stages 1, 2, 3, or 4), poor sleep efficiency (sleep efficiency=((time asleep/ opportunity to sleep)*100), wake after sleep onset (WASO; measured in minutes awake after falling into persistent sleep or the fraction of time awake from persistent sleep until "lights on"), and extended latency to persistent sleep (LPS; time between "lights off" and onset of persistent sleep).

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:
1. An isolated compound of formula II

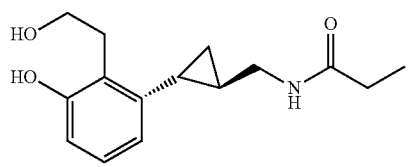

Formula II or a salt, stereoisomer, solvate, or hydrate thereof, in amorphous or crystalline form.

2. An isolated compound of formula III

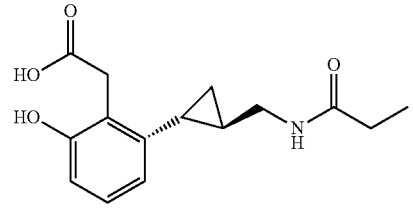

Formula III or a salt, stereoisomer, solvate, or hydrate thereof, in amorphous or crystalline form.

3. A pharmaceutical composition comprising:
at least one compound selected from the group consisting of: a compound of Formula II, a compound of Formula III, and salts, stereoisomers, solvates, and hydrates thereof, in amorphous or crystalline form

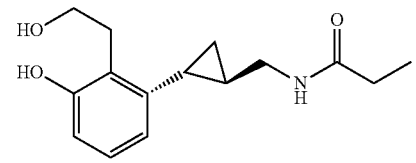

Formula II

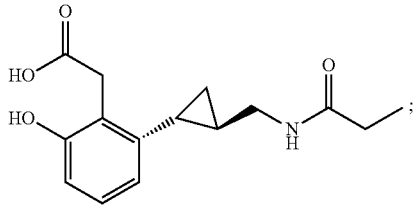

Formula III and
and a pharmaceutically-acceptable carrier.

4. The composition of claim 3, in unit dosage form, wherein 1 to 4 such unit dosage forms comprise at least one compound in a therapeutically-effective amount for the treatment of at least one of the following: a circadian rhythm disorder, a disorder with a circadian component, or a sleep disorder.

5. The composition of claim 4, wherein the amount is effective for the treatment of a sleep disorder selected from the group consisting of: insomnia, poor total sleep time, wake after sleep onset (WASO), poor sleep efficiency, and extended latency to persistent sleep (LPS).

6. The composition of claim 4, wherein the amount is effective for the treatment of a circadian rhythm disorder or disorder with a circadian component selected from the group consisting of: jet lag, shift worker sleep disorder (SWSD), General Anxiety Disorder, Major Depressive Disorder, Seasonal Affective Disorder, Attention Deficit/Hyperactivity Disorder, Alzheimers Disease, Angelman Syndrome, Bipolar Disorder, Schizophrenia, Autism, Epilepsy, Migraine, night-time hypertension, obesity and/or type 2 diabetes, and testosterone insufficiency.

7. The composition of claim 3, formulated for administration via at least one route selected from a group consisting of:

oral, parenteral, intravenous, intramuscular, buccal, lozenge, transdermal, and transmucosal.

8. The composition of claim 7, formulated for oral administration.

9. The composition of claim 8, wherein the at least one compound is present in an amount between about 5 mg and about 100 mg.

10. The composition of claim 8, wherein the at least one compound is present in an amount equivalent to a dosage of between about 1 mg/day and about 500 mg/day.

11. The composition of claim 10, wherein the dosage is between about 10 mg/day and about 100 mg/day.

12. The composition of claim 11, wherein the dosage is about 20 mg/day.

* * * * *